US007261861B2

(12) United States Patent
Kautzky

(10) Patent No.: US 7,261,861 B2
(45) Date of Patent: Aug. 28, 2007

(54) HEMOSTASIS ANALYZER AND METHOD

(75) Inventor: Hans Kautzky, West Chicago, IL (US)

(73) Assignee: Haemoscope Corporation, Niles, IL (US)

( * ) Notice: Subject to any disclaimer, the term of this patent is extended or adjusted under 35 U.S.C. 154(b) by 515 days.

(21) Appl. No.: 10/422,229

(22) Filed: Apr. 24, 2003

(65) Prior Publication Data

US 2004/0214337 A1 Oct. 28, 2004

(51) Int. Cl.
*G01N 33/86* (2006.01)

(52) U.S. Cl. ............... 422/73; 436/69; 73/64.41

(58) Field of Classification Search .......... 73/64.41; 422/73; 436/69
See application file for complete search history.

(56) References Cited

U.S. PATENT DOCUMENTS

| | | | | |
|---|---|---|---|---|
| 3,854,324 A | * | 12/1974 | Altshuler et al. | 73/64.42 |
| 4,149,405 A | * | 4/1979 | Ringrose | 73/54.01 |
| 4,202,204 A | * | 5/1980 | Hartert | 73/64.42 |
| 4,341,111 A | * | 7/1982 | Husar | 73/64.42 |
| 4,695,956 A | | 9/1987 | LeVeen et al. | |
| 5,075,077 A | * | 12/1991 | Durley et al. | 422/56 |
| 5,096,669 A | | 3/1992 | Lauks et al. | 442/61 |
| 5,100,805 A | * | 3/1992 | Ziege et al. | 436/517 |
| 5,114,860 A | | 5/1992 | Hayashi | 436/69 |
| 5,167,145 A | | 12/1992 | Butler et al. | |
| D337,164 S | | 7/1993 | Lauks et al. | D24/223 |
| 5,416,026 A | | 5/1995 | Davis | 436/66 |
| 5,447,440 A | | 9/1995 | Davis et al. | 435/6 |
| 5,534,226 A | | 7/1996 | Gavin et al. | 422/73 |
| 5,580,744 A | | 12/1996 | Zweig | 435/13 |
| 5,628,961 A | | 5/1997 | Davis et al. | 422/63 |
| 6,060,323 A | | 5/2000 | Jina | |
| 6,066,504 A | | 5/2000 | Jina | 436/69 |
| 6,136,271 A | | 10/2000 | Lorincz et al. | 422/73 |
| 6,196,979 B1 | | 3/2001 | Virtanen | 600/573 |
| 6,200,532 B1 | | 3/2001 | Wu et al. | 422/73 |
| 6,327,031 B1 | | 12/2001 | Gordon | 356/72 |
| 6,338,821 B1 | | 1/2002 | Jina | 422/73 |
| 6,438,498 B1 | | 8/2002 | Opalsky et al. | 702/25 |
| 6,524,861 B1 | | 2/2003 | Anderson | |

FOREIGN PATENT DOCUMENTS

WO    WO-01/96879 A2    12/2001

OTHER PUBLICATIONS

Voleisis et al., "Ultrasonic method for the whole blood coagulation analysis," Ultrasonics, vol. 40, May 2002, pp. 101-107.
Partial International Search Report for Application No. PCT/US2004/012833 dated Oct. 8, 2004.

* cited by examiner

*Primary Examiner*—Jill Warden
*Assistant Examiner*—Paul S Hyun
(74) *Attorney, Agent, or Firm*—Marshall, Gerstein & Borun LLP

(57) ABSTRACT

A method and device for blood hemostasis analysis is disclosed. A blood sample is displaced to reach a resonant state. The resonant frequency of the blood sample is determined before, during and after a hemostasis process. The changes in the resonant frequency of the blood sample are indicative of the hemostasis characteristics of the blood sample.

10 Claims, 8 Drawing Sheets

HEMOSTASIS ANALYZER AND METHOD

FIELD OF THE DISCLOSURE

This disclosure relates generally to blood analysis, and more particularly, to a blood hemostasis analyzer and method.

BACKGROUND

Blood is in liquid form when traveling undisturbed in bodily passageways. However, an injury may cause rapid clotting of the blood at the site of the injury to initially stop the bleeding, and thereafter, to help in the healing process. An accurate measurement of the ability of a patient's blood to coagulate in a timely and effective fashion and to subsequent lysis is crucial to certain surgical and medical procedures. Also, accurate detection of abnormal hemostasis is of particular importance with respect to appropriate treatment to be given to patients suffering from clotting disorders.

Blood hemostasis is a result of highly complex biochemical processes that transform the blood from a liquid state to a solid state. Characteristics of blood, such as strength of the clot, infer that the mechanical properties of the blood are important in determining characteristics rather than the viscosity of the blood when in a liquid state.

DETAILED DESCRIPTION

Figure 1:
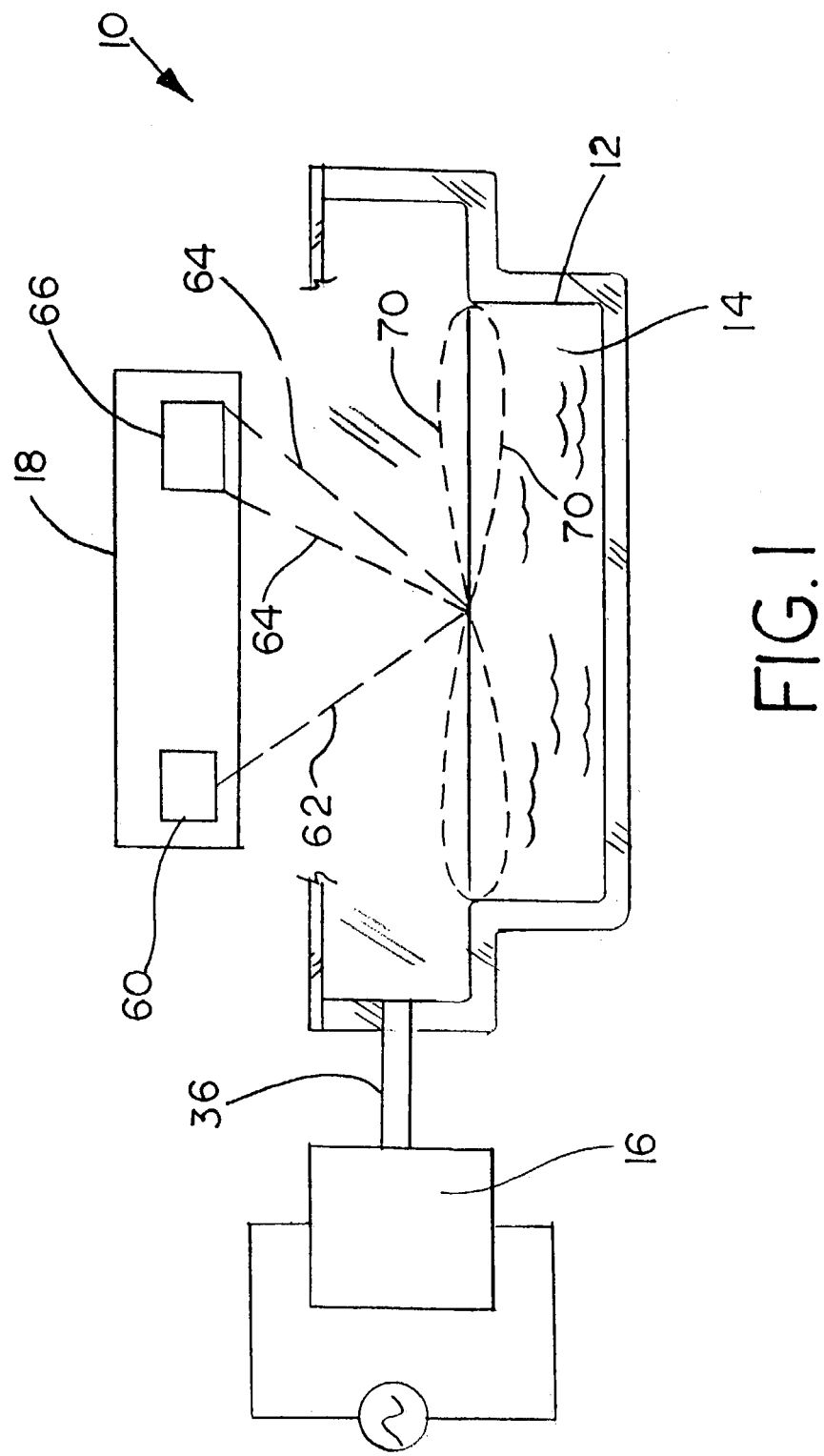
FIG. 1 is a schematic diagram of a blood hemostasis analyzer constructed in accordance with the teachings of the instant disclosure.

Referring to FIG. 1, a blood hemostasis analyzer 10 in accordance with the teachings of the instant disclosure is generally shown. The analyzer 10 operates under the principle that because hemostasis of a blood sample changes the blood sample from a liquid state to a gel-like state, and the modulus of elasticity of the blood sample controls the natural frequency of the blood sample, measuring the changes in the natural frequency of the blood sample during hemostasis provides the hemostasis characteristics of the blood sample. In keeping with this principle, the disclosed blood hemostasis analyzer 10 measures the changes in the fundamental natural frequency of a blood sample during hemostasis and lysis processes to provide hemostasis characteristics of the blood sample. To practice the foregoing principal, the analyzer 10 generally includes a container 12 for holding a blood sample 14, a shaker 16 for displacing the container 12 to thereby excite the blood sample 14 to a resonant vibration, and a sensor 18 for measuring the resulting amplitude of the blood sample 14.

An exemplary method by which the disclosed blood hemostasis analysis is performed will now be described. Vibration of a liquid at resonance closely resembles sloshing, which is analogous to the motion of a pendulum. Accordingly, as blood transitions from a liquid state to a gel-like state and possibly to a solid state during clotting, the fundamental natural frequency of the blood increases. The disclosed exemplary method measures the changes in the fundamental natural frequency of the blood sample 14 during hemostasis/clotting and lysis processes.

Initially, a blood sample 14 is placed in the container 12. The container 12 is then vibrated by the shaker 16 so that the blood sample 14, which is initially in a liquid state, is vibrating in a linear sloshing mode. A liquid typically vibrates near its first fundamental natural frequency in a sloshing mode, which can be defined as the swinging of the entire mass of the liquid in a container, hence the analogy to a pendulum. The amplitude of the sloshing reaches maximum when the blood sample 14 is vibrated at its fundamental natural frequency. Thus, to initially excite the blood sample 14 to resonance, the shaker 16 vibrates the container 12 at or very near the fundamental natural frequency of the blood sample 14. Furthermore, the shaker 16 vibrates the container 12 at or very near the fundamental natural frequency of the blood sample 14 as this frequency changes throughout the hemostasis and possibly lysis processes.

One of ordinary skill in the art will readily appreciate the numerous methods by which the shaker 16 can vibrate the container 12 at or near the fundamental natural frequency of the blood sample 14 throughout the hemostasis and lysis processes. However, in the disclosed example, the container 12 is initially vibrated at a frequency below the fundamental natural frequency of the blood sample 14. The frequency is then increased in small steps, and concurrently, the resulting displacement amplitudes of the blood sample 14 are measured. As the frequency of vibration of the container 12 increases to near the blood sample's fundamental natural frequency, the displacement amplitude of the blood sample 14 will dramatically increase. The displacement amplitude of the blood sample 14 will reach maximum at its fundamental natural frequency. Thus, monitoring the displacement amplitude of the blood sample 14 for a maximum provides a value for the fundamental natural frequency of the blood sample 14 when that maximum is reached.

Figure 2:
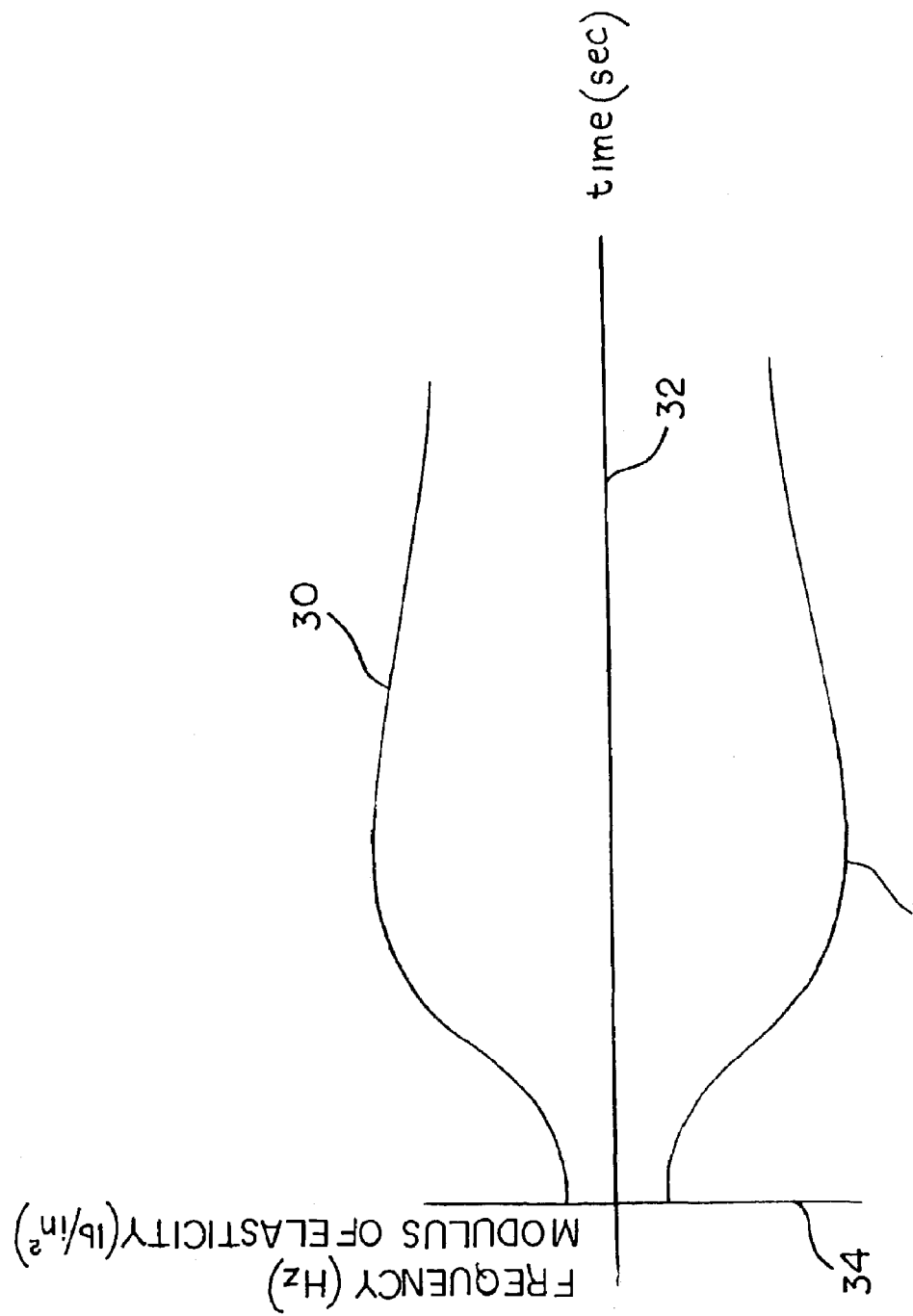
FIG. 2 is a graph representing hemostasis characteristics of a blood sample in accordance with the teachings of the instant disclosure.

As the hemostasis process continues, the foregoing method of finding the fundamental natural frequency of the blood sample 14 is repeated. The measured fundamental natural frequencies of the blood sample 14 when plotted vs. time result in a curve 30 similar to that shown in FIG. 2. Curve 30 is typically represented with its mirror image relative to the x-axis, which is shown as curve 31. The shape of the curve 30 is indicative of blood hemostasis characteristics. The x-axis 32 represents time, while the y-axis 34 represents the fundamental natural frequency of the blood sample 14 during the hemostasis and lysis processes. One of ordinary skill in the art will appreciate that since frequency of the blood sample 14 is proportional to the modulus of elasticity of the blood sample 14, the y-axis also represents the changes in the modulus of elasticity of the blood sample 14 during hemostasis and lysis processes.

One of ordinary skill in the art will readily appreciate that the size of the frequency step by which the vibration frequency of the container 12 is increased or decreased during testing will affect how quickly and efficiently the fundamental natural frequency of the blood sample 14 is pinpointed. For instance, a very large frequency step may not provide a detailed frequency resolution to locate a near accurate measure of the fundamental natural frequency of the blood sample 14. On the other hand, a very small frequency step may not provide a rapid approach to pinpointing the fundamental natural frequency of the blood sample 14. Accordingly, in order to find the fundamental natural frequency of the blood sample within the frequency range by which the container 12 is vibrated, it may be necessary to search for the fundamental natural frequency of the blood sample 14 by changing the frequency step and/or adding or subtracting the frequency step from the vibration frequency of the container 12 in a methodical manner. Numerous mathematical algorithms and methods are well known to those of ordinary skill in the art, by which the frequency step can be methodically varied to provide a rapid pinpointing of a peak in amplitude of oscillation of the blood sample 14.

One of ordinary skill in the art can use other well known methods for finding the fundamental natural frequency of the blood sample throughout the hemostasis and lysis processes. For example, displacing the container 12 with a frequency function that emulates white noise having frequency components near or equal to the fundamental natural frequencies of the blood sample 14 throughout the hemostasis and lysis processes can excite the blood sample 14 to a resonant state. White noise is a frequency function that includes frequency components selected within a range of frequencies. Because the blood sample will respond with resonant excitation to a frequency that is equal or near its fundamental natural frequency, a white noise having such a frequency component will excite the blood sample 14 to a resonant state. One of ordinary skill in the art will readily appreciate that well known methods such as Fourier Frequency Analysis can be utilized to find the fundamental frequency of the blood sample 14 after being excited by white noise.

An exemplary device employing the foregoing method of determining hemostasis characteristics of a blood sample 14 will now be described. Referring to FIG. 1, the shaker 16 displaces the container 12 to excite the blood sample 14 to resonant vibration. Generally, the shaker 16 is a device capable of oscillating the container 12 with a desired frequency and amplitude. One of ordinary skill in the art will appreciate the numerous devices by which an object can be oscillated. In the disclosed example, the shaker 16 is a dipcoil, which is similar to a voice coil of a speaker. In other words, the shaker 16 includes an electromagnet that oscillates relative to a stationary permanent magnet by having its current driven by an electrical signal. The shaker 16 may be connected either directly or with a connecting link 36 to the container 12. The connecting link 36 transfers the motion created by the shaker 16 to the container 12. As is well known to those of ordinary skill in the art, characteristics of the electrical signal, i.e., voltage, current, direction of current, etc., determine the characteristics of the oscillatory motion of the shaker 16. Accordingly, the shaker 16 can displace the container 12 with any desired amplitude and frequency within the operational limits of the shaker 16.

The container 12 holds the blood sample 14 during the excitation of the blood sample 14. The container 12 may be any shape or size. However, the shape and size of the container may affect the operation of the analyzer 10, because the container 12 acts as a resonator. The larger the container 12, the lower the natural frequency of the blood sample 14 will be. Furthermore, the container 12 cannot be too small so that a meniscus effect is produced due to the surface tension in the blood sample 14. Conversely, if the container 12 is too large, a large blood sample 14 will be needed for the analysis in the analyzer 10, which may not be medically acceptable.

Figure 3:
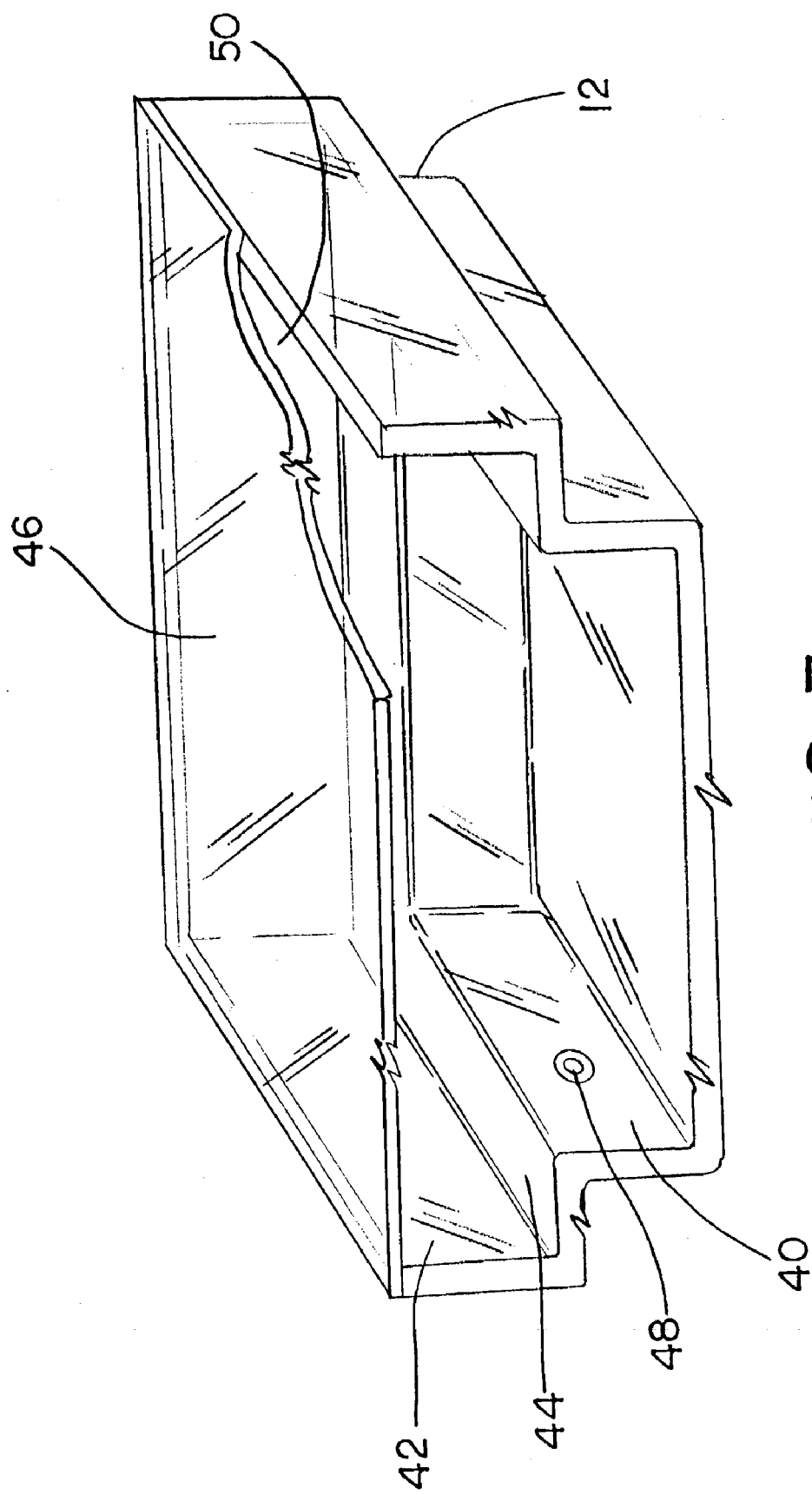
FIG. 3 is a perspective and exploded sectional view of a container for holding a blood sample in accordance with the teachings of the instant disclosure.

An exemplary container 12 is shown in FIG. 3. The container 12 has a lower portion 40 and an upper portion 42. The lower portion 40 and the upper portion 42 are generally rectangular. The upper portion 42 has a larger width, a larger length, and a smaller depth than the lower portion 40, so as to provide an internal step 44. The container 12 also includes a lid 46 that is sealably attached to the top of the upper section 40. The container 12 includes a port 48 for receiving a blood sample 14. To reduce the meniscus effect of the blood sample 14 when placed in the container 12, the lower portion 40 is filled with the blood sample up to where the upper portion 42 begins. Accordingly, the volume of the blood sample 14 is substantially equal to the volume of the lower portion 40.

To prevent the blood sample 14 from evaporating during testing and to prevent contamination thereof, the port 48 may be self sealing. For example, the port 48 may be constructed from rubber or silicon so that when a syringe needle is inserted therein, the rubber or silicon resiliently surrounds the syringe needle to substantially seal the port during the injection of the blood sample 14 into the container 12. When the needle is withdrawn from the port 48, resilience of the rubber or the silicon substantially re-seals the hole created by the needle. To prevent evaporation of the blood sample 14 and any reaction the blood sample may have by being exposed to air, the container 12 can be pre-filled or pressurized with an inert gas, such as Helium. Alternately, the air in the container can be removed to provide a vacuum inside the container 12. One of ordinary skill in the art will recognize that the pressure in the container 12 has minimal to no effect on the fundamental natural frequency of the blood sample 14. In the example disclosed herein, the container 12 is safely disposable and can be safely discarded after each use. The disposability of the container 12 ensures that the blood sample 14 is safely handled during testing and safely discarded after testing. In addition, the disposable container 12 can be manufactured to be completely sealed and only provide access thereto by the port 48. Thus, the disposability of the container 12, combined with the container 12 being completely sealed, ensure that the blood sample 14 is not exposed to air (i.e., to prevent the drying of the surface of the blood sample 14) or any other contaminants, and furthermore, ensure safety in handling and disposing of the blood sample 14 before, during, and after testing.

The analyzer 10 includes a slot (not shown) to receive the container 12. One of ordinary skill in the art will readily appreciate that the container 12 may be inserted in and removed from the slot in any manner desirable. However, to provide easy insertion and removal of the container 12 from the analyzer 10, the container 12 may include a handle (not shown) that can be held by a user for insertion and removal of the container 12 to and from the analyzer 10, respectively.

To measure oscillations of the blood sample 14 as a result of the displacement of the container 12, a fixed electromagnetic source 60 emits a beam 62 toward the blood sample 14. As shown in FIG. 1, the source 60 may be part of the sensor 18 (i.e., an active sensor). Alternatively, the source 60 and a sensor 66 (i.e., a passive sensor) can be independent devices. The beam 62 is detected by the sensor 18 after being reflected from the surface of the blood sample 14. The characteristics of the beam after being reflected from the surface of the blood sample 14 are indicative of the movement of the blood sample 14 in response to displacements of the container 12.

One of ordinary skill in the art will appreciate that the electromagnetic beam of the source 60 may be produced by any emission within the electromagnetic spectrum so long as the beam 62 can reflect from the surface of the blood sample 14, and the beam's characteristics after reflecting from the surface of the blood sample 14 indicate the movement of the blood sample 14.

In the disclosed example, the source 60 is a fixed LED (Light Emitting Diode) source that directs a beam 62 towards the blood sample 14. The beam 62 is then reflected from the surface of the blood sample 14. Accordingly, the container 12 has an optically transparent portion so that the beam 62 and its reflection 64 can enter and exit the container 12, respectively. In the disclosed example, the lid 46 is transparent to light. One of ordinary skill in the art will recognize that the lid 46, although transparent, will itself reflect some of the light in the beam 62. To reduce the reflection of light from the lid 46, an anti-reflective coating may be applied to the lid 46. Such anti-reflective coatings are well known to those of ordinary skill in the art as they are applied to a variety of optical devices, such as eyeglasses, telescopes, cameras, etc. Although most liquids are highly transparent to light, the surface of blood forms a highly reflective surface so that most of the beam 62 is reflected from the surface of the blood sample 14.

Figure 4:
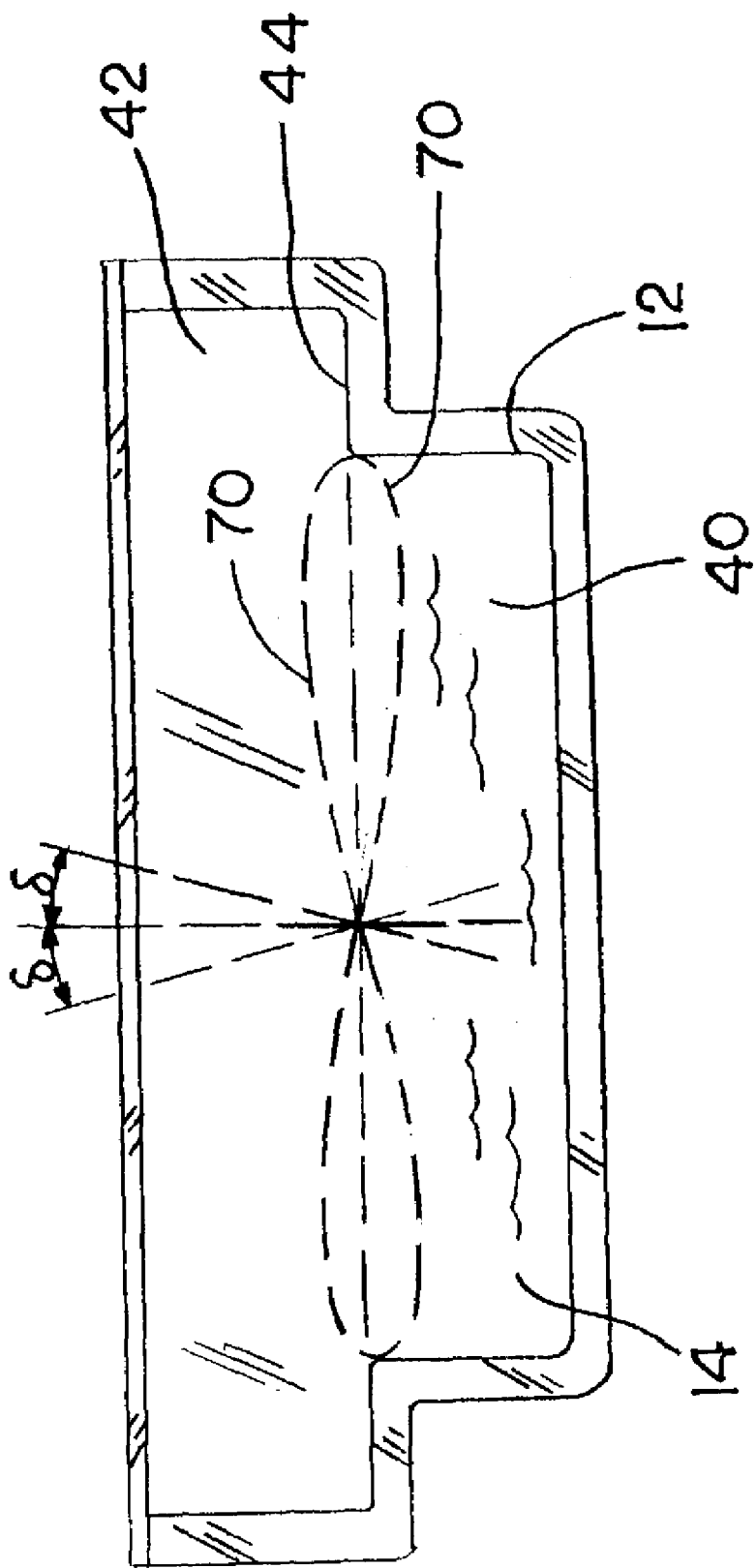
FIG. 4 is a schematic view of the container of FIG. 3 having therein a blood sample and vibrating the blood sample in accordance with the teachings of the instant disclosure.

Referring to FIG. 4, the displacements of the blood sample 14 relative to a rest position are shown with dashed lines 70 having an angle δ. Accordingly, the displacement of the blood sample 14 changes the angle of the reflection 64 of the beam 62 by the same angle δ. The sensor 18 intercepts the reflection 64 of the beam 62 from the surface of the blood sample 14 and produces an electric signal indicative of the displacement of the blood sample 14. In the disclosed example, the sensor 18 includes a plurality of photo diodes that collectively detect the displacement of the reflection of the beam 64. The outputs of the diodes are measured differentially so that peaks in the displacement of the blood sample 14, which are indicative of resonance, can be identified.

Figure 5:
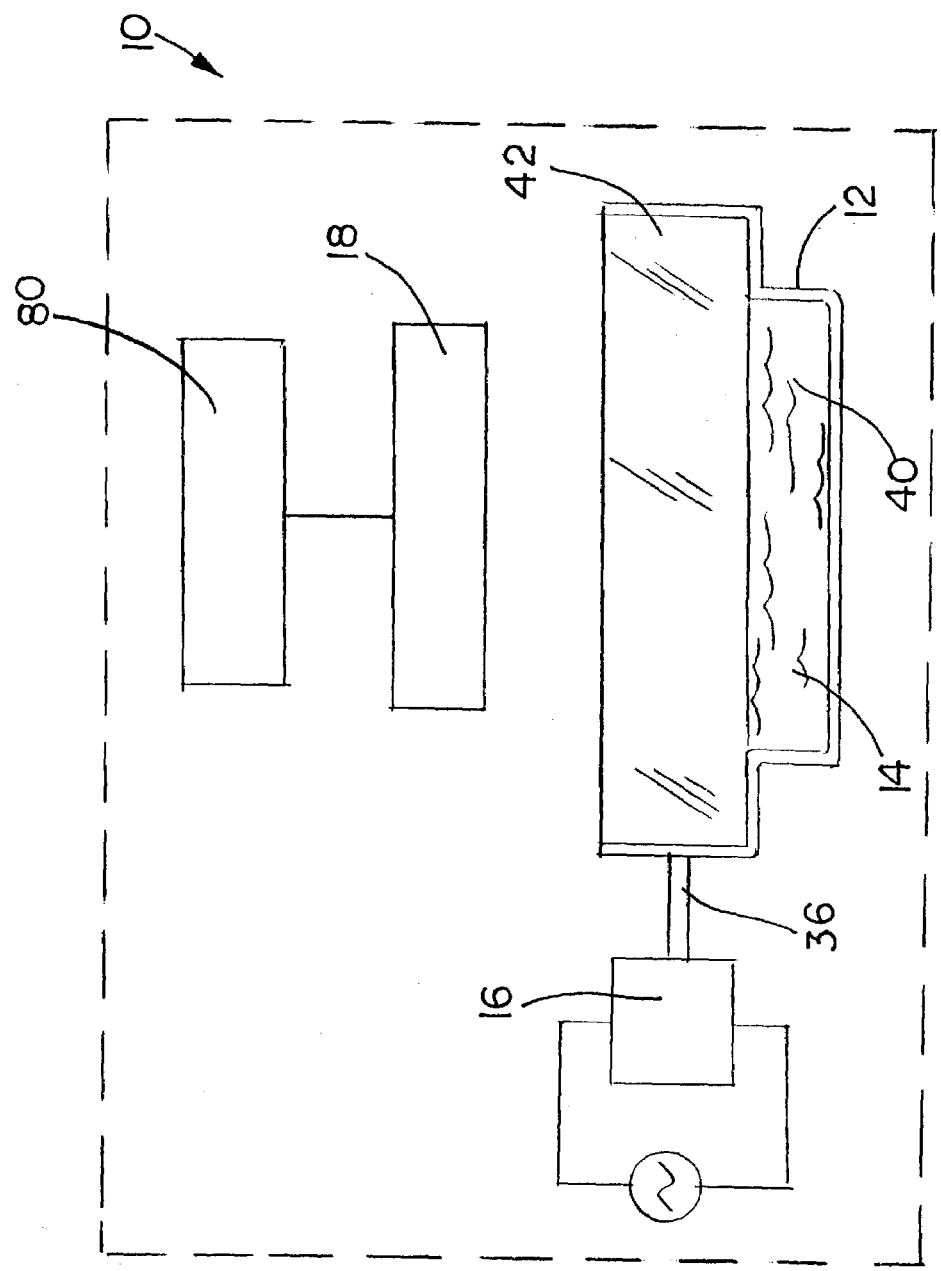
FIG. 5 is a schematic view of an analyzer in accordance with the teachings of the instant disclosure.
Figure 6:
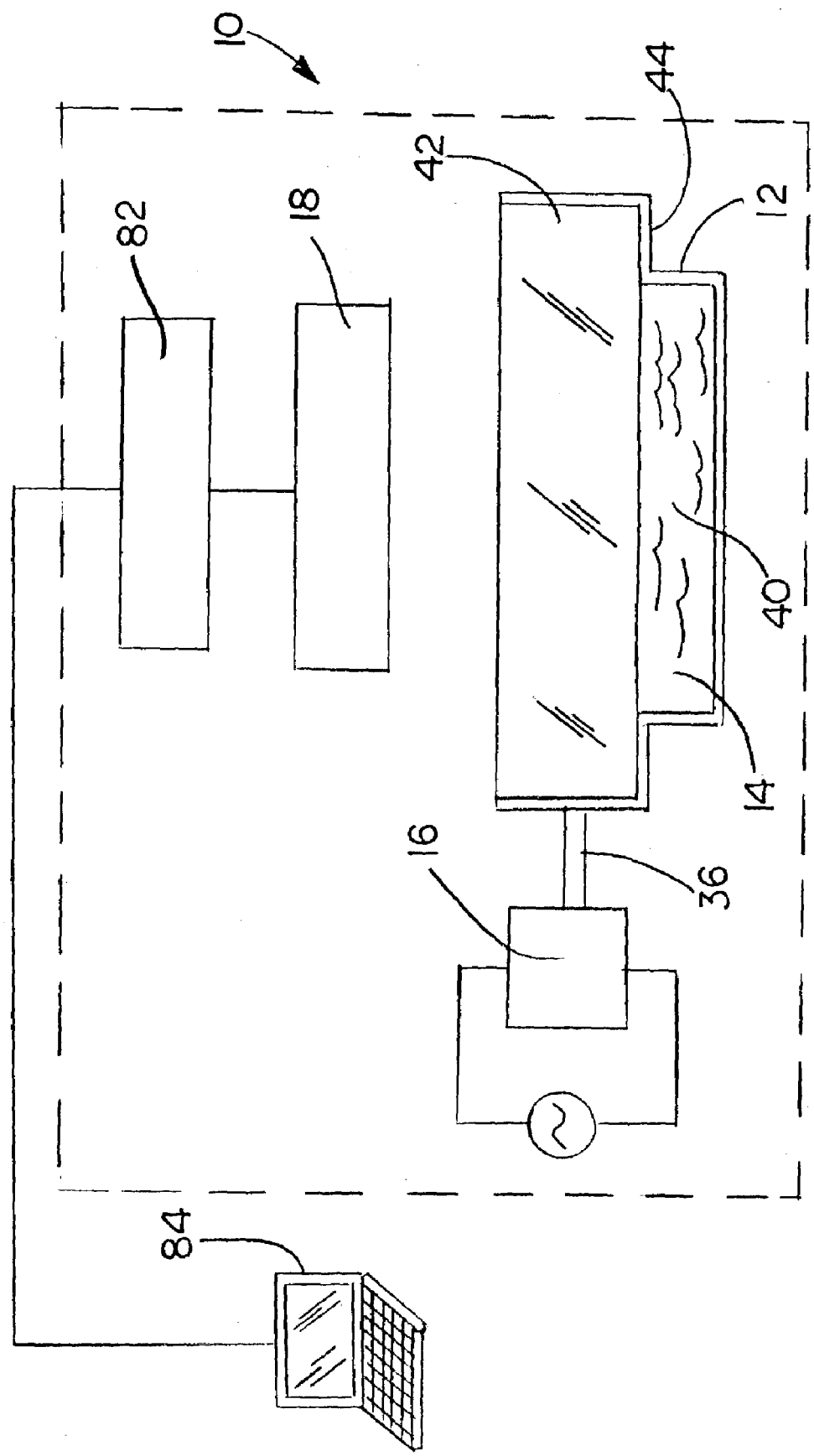
FIG. 6 is a schematic view of an analyzer in accordance with the teachings of the instant disclosure.
Figure 7:
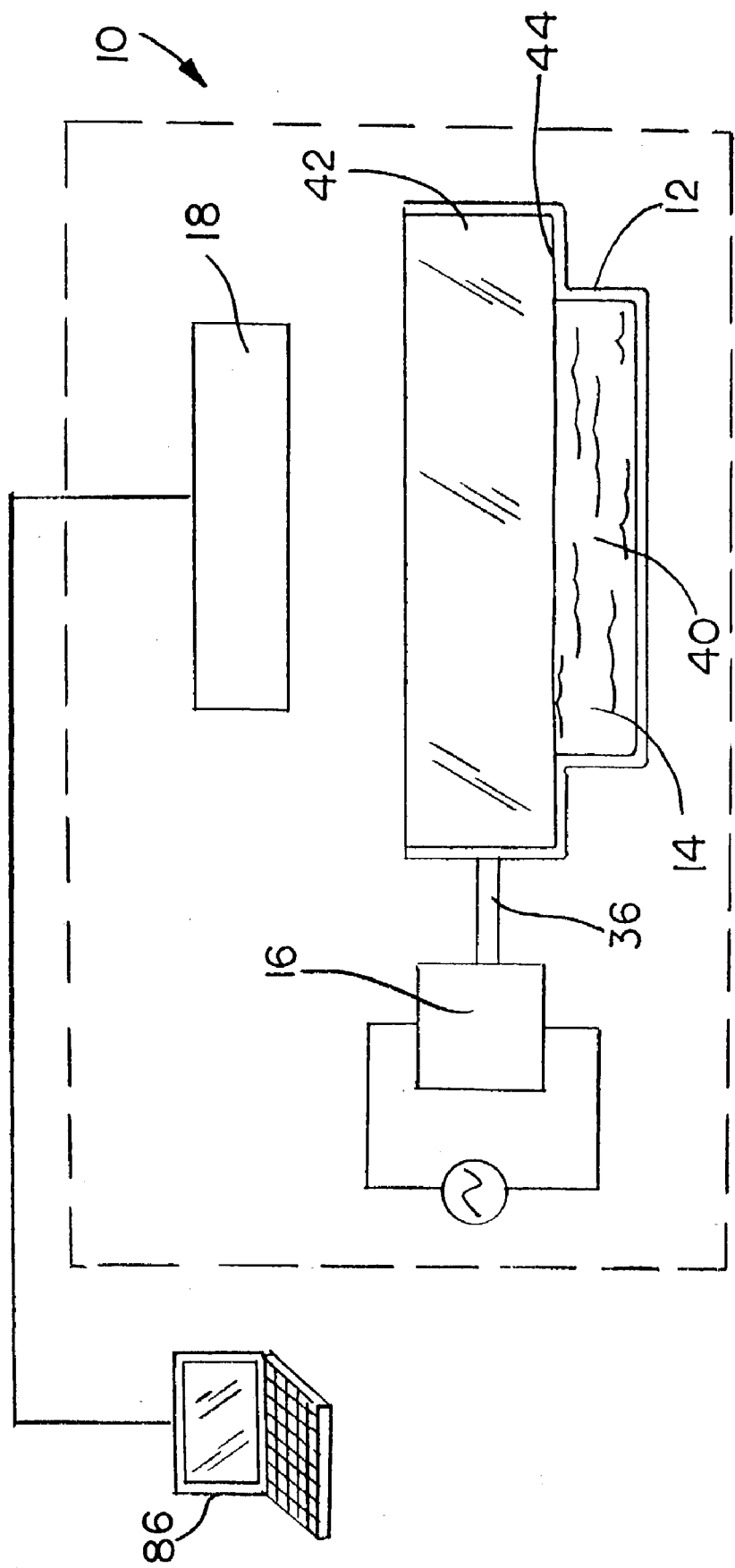
FIG. 7 is a schematic view of an analyzer in accordance with the teachings of the instant disclosure.

In others example of the present disclosure, the vibrations in the blood sample 14 may be measured by a number of other devices. In one example, acoustic sensors (not shown) disposed in the container 12 can differentially measure the distance from the surface of the blood sample 14 to the sensor, which is indicative of the vibration in the blood sample 14. In another example, electrodes (not shown) arranged in the container 12 function as either a capacitive or resistive bridge (i.e., a Wheatstone bridge). The voltage differential of the capacitors or the resistors is indicative of the vibrations of the blood sample 14. In yet another example, two photo diodes (not shown) can be placed on an interior wall of the container near the surface of the blood sample 14. As the blood sample 14 vibrates, it partially or fully obscures one or both of the diodes (i.e., preventing light from reaching the diodes). Accordingly, the outputs of the diodes are measured differentially so that peaks in the displacement of the blood sample 14, which are indicative of resonance, can be identified One of ordinary skill in the art will appreciate the numerous methods and devices that can be used for driving the shaker 16 and analyzing the signals from the sensor 18 for determining the hemostasis characteristics of the blood sample 14. For instance, as shown in FIG. 5, the blood hemostasis analyzer 10 can include an internal computing device 80 that includes the necessary hardware and software to drive the shaker 16 independently or in response to signals from the sensor 18. Furthermore, the internal computing device 80 can analyze the signals from the sensor 18 to determine the fundamental natural frequencies of the blood sample 14 during hemostasis. As described in the foregoing, such an analysis will yield data for constructing the curves 30 and other data regarding the hemostasis characteristics of the blood sample 14. In another example as shown in FIG. 6, the analyzer 10 can include a memory device 82 for storing the data from the sensor 18 for later analysis by an external computing device 84. The shaker 10 can be driven by a predetermined method stored in the memory device 82, or by the external computing device 84. In yet another example shown in FIG. 7, the analyzer 10 does not include any internal memory or computing device. During testing, the analyzer 10 is in continuous and real-time communication with an external computing device 86 (e.g., laptop, personal digital assistant, desktop computer, etc.). The external computing device 86 drives the shaker 16 and receives signals from sensor 18 to determine the hemostasis characteristics of the blood sample 14 as described in the foregoing. One of ordinary skill in the art will appreciate that numerous other well known methods, algorithms and devices can be utilized to drive the shaker 16, independently or in response to signals from the sensor 18, and determine blood hemostasis characteristics from the sensor signals. Furthermore, the determined blood hemostasis characteristics can be conveyed to a user by a variety of well known methods and devices, such as displaying data on a display screen, or printing the results on paper.

One of ordinary skill in the art will appreciate that the foregoing generalized device is very rugged and not easily susceptible to damage from being mishandled. The disclosed device has a very small number of moving parts or parts that are breakable. Furthermore, the simplicity of the disclosed device provides for quick replacement of a defective part when necessary.

Figure 8:
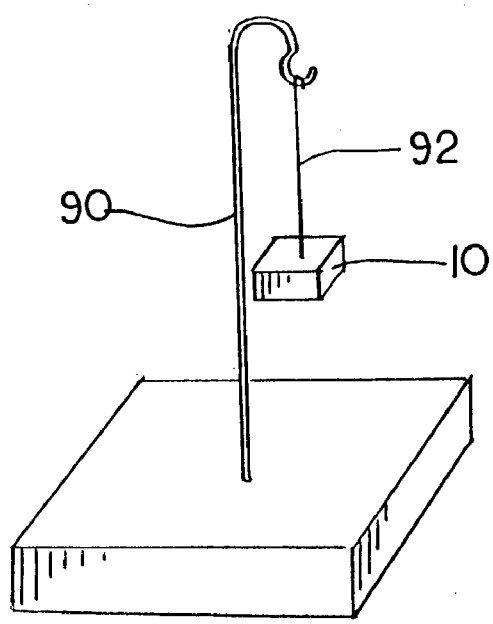
FIG. 8 is a perspective view of a first exemplary stand for a blood hemostasis analyzer constructed in accordance with the teachings of the instant disclosure.
Figure 9:
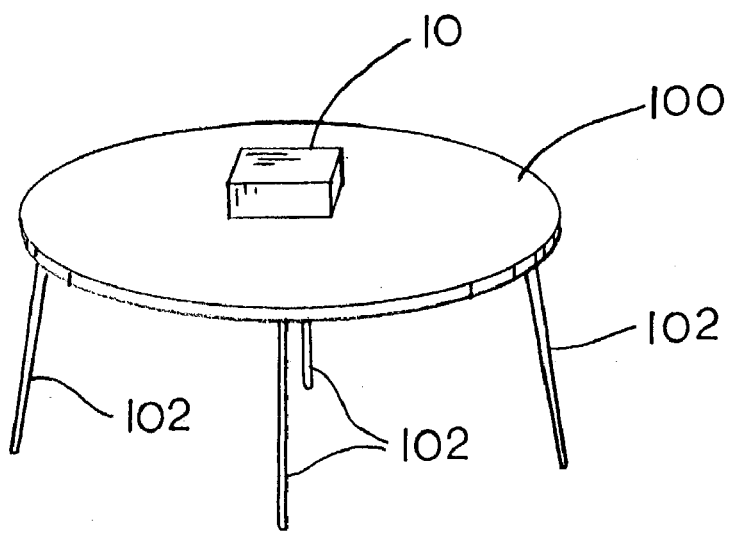
FIG. 9 is a perspective view of a second exemplary stand for a blood hemostasis analyzer constructed in accordance with the teachings of the instant disclosure.

Ambient vibrations or seismic noise near the analyzer 10 can disturb or influence the blood hemostasis analysis. Accordingly, the analyzer 10 can include a vibration filtering device onto which the analyzer 10 is mounted. In a first example as shown in FIG. 8, the vibration filtering device is a hook 90, from which the analyzer 10 is suspended by a cable 92. In effect, the analyzer 10 is suspended from the hook 90 in a pendulum-like manner. Seismic noise or ambient vibration in a wide range of frequencies is dissipated through the hook 90 and the cable 92 prior to reaching the analyzer 10. One of ordinary skill in the art will appreciate that any wire that is connected to the analyzer 10 for power or communication purposes can be carried by the cable 92 so as to not externally influence the motion of the analyzer 10 (e.g., hanging wires contacting other objects). In a second example as shown in FIG. 9, the seismic filtering device is a platform 100 that rests on a number of legs 102. In effect, the platform 100 is an inverted pendulum. In application, the analyzer 10 is placed on the platform 100 so that any ambient vibration or seismic noise within a wide frequency range is dissipated through the platform 100 prior to reaching the analyzer 10. One of ordinary skill in the art will appreciate many other ways of isolating noise, including use of vibration absorbing foams, spring suspension and the like.

Although certain apparatus constructed in accordance with the teachings of the invention have been described herein, the scope of coverage of this patent is not limited thereto. On the contrary, this patent covers all examples of the teachings of the invention fairly falling within the scope of the appended claims either literally or under the doctrine of equivalents.

The invention claimed is:

1. An apparatus for measuring hemostasis comprising:
   a. a container adapted to hold a blood sample, the container including a portion transparent to an emission from a sensor;
   b. a shaker adapted to displace the container in order to cause a resonant excitation of the blood sample, the blood sample being excited to a resonant state; and
   c. the sensor adapted to determine a movement of the blood sample corresponding to the resonant excitation of the blood sample within the container responsive to the displacement of the container by the shaker by generating the emission and directing the emission toward the blood sample through the portion;
   d. wherein data from the sensor is indicative of the resonant state of the blood sample and the shaker is configured to displace the container at a displacement frequency and configured to vary the displacement frequency responsive to changes in the resonant state of the blood sample.

2. An apparatus according to claim 1, further comprising an analyzer coupled to the sensor to receive the data from the sensor, the analyzer being adapted to derive a hemostasis characteristic of the blood sample based upon the data from the sensor.

3. An apparatus according to claim 1, wherein the shaker is configured to displace the container with a white noise frequency function.

4. An apparatus according to claim 1, wherein the container includes a self-sealing port for receiving the blood sample.

5. An apparatus according to claim 1, wherein the container is a sealed container.

6. An apparatus according to claim 1, wherein the container is safely disposable.

7. An apparatus according to claim 1, wherein the container comprises a first portion connected to a larger second portion, wherein the blood sample fills the first portion.

8. An apparatus according to claim 1, wherein the sensor is an optical sensor.

9. An apparatus for measuring hemostasis comprising:
   a. a slot for receiving a container having therein a blood sample, wherein a portion of the container is transparent to an emission from a sensor;
   b. a shaker adapted to displace the container in order to cause an excitation of the blood sample, the blood sample being excited to a resonant state;
   c. the sensor adapted to determine a movement of the blood sample within the container responsive to the displacement of the container by the shaker by generating the emission and directing the emission toward the blood sample through the portion; and
   d. an analyzer coupled to the sensor to receive data from the sensor, the analyzer being adapted to derive a hemostasis characteristic of the blood sample based upon the data from the sensor;
   e. wherein data from the sensor is indicative of the resonant state of the blood sample and the shaker is configured to displace the container at a displacement frequency and configured to vary the displacement frequency responsive to changes in the resonant state of the blood sample.

10. An apparatus according to claim 9, wherein the shaker is configured to displace the container with a white noise frequency function.

* * * * *